United States Patent
Schalitz et al.

(10) Patent No.: US 6,180,585 B1
(45) Date of Patent: Jan. 30, 2001

(54) AQUEOUS DISINFECTANT AND HARD SURFACE CLEANING COMPOSITION AND METHOD OF USE

(75) Inventors: William John Schalitz, Whitehouse; Jason J. Welch, Perrysburg; Ronald Thomas Cook, Bowling Green, all of OH (US)

(73) Assignee: Spartan Chemical Company, Inc., Toledo, OH (US)

( * ) Notice: Under 35 U.S.C. 154(b), the term of this patent shall be extended for 0 days.

(21) Appl. No.: 09/293,243

(22) Filed: Apr. 16, 1999

(51) Int. Cl.$^7$ ............................... C11D 1/62; C11D 3/386
(52) U.S. Cl. .................. 510/384; 510/195; 510/199; 510/226; 510/238; 510/300; 510/305; 510/319; 510/362; 510/382; 510/391; 510/392; 510/530
(58) Field of Search ...................... 510/195, 199, 510/226, 238, 300, 305, 319, 362, 382, 384, 391, 392, 530

(56) References Cited

U.S. PATENT DOCUMENTS

| | | |
|---|---|---|
| H1776 | 1/1999 | Linard et al. . |
| 4,088,596 * | 5/1978 | Arai et al. ............................. 252/99 |
| 4,404,128 | 9/1983 | Anderson . |
| 4,655,794 * | 4/1997 | Richardson . |
| 4,839,373 | 6/1989 | Ito et al. . |
| 4,866,081 | 9/1989 | Ito et al. . |
| 4,898,781 * | 2/1990 | Onouchi et al. ............... 428/402.22 |
| 5,055,219 * | 10/1991 | Smith .................................. 252/102 |
| 5,342,525 * | 8/1994 | Rowsell .............................. 210/611 |
| 5,409,546 | 4/1995 | Nakagawa et al. . |
| 5,449,619 * | 9/1995 | Griffin et al. ....................... 435/264 |
| 5,624,891 * | 4/1997 | Smialowicz et al. ............... 510/195 |
| 5,731,278 | 3/1998 | Nair et al. . |
| 5,780,023 | 7/1998 | McLaughlin et al. . |
| 5,783,537 * | 7/1998 | Ahmed et al. ...................... 510/193 |
| 5,786,316 * | 7/1998 | Baeck et al. ....................... 510/235 |
| 5,797,986 | 8/1998 | Rolando et al. . |
| 5,837,010 * | 11/1998 | Baeck et al. ........................... 8/137 |
| 5,863,882 * | 1/1999 | Lin et al. ............................ 510/397 |
| 5,935,271 * | 8/1999 | Lappas et al. .......................... 8/137 |

FOREIGN PATENT DOCUMENTS

| | | |
|---|---|---|
| WO97/25865 | 7/1997 | (WO) . |
| WO97/16541 | 9/1997 | (WO) . |
| WO 97/38586 | 10/1997 | (WO) . |
| WO 99/16854 | 4/1999 | (WO) . |

OTHER PUBLICATIONS

"New Oral Drug May Treat Colon Infections." *Doctor's Guide To Medical & Other News* (1997) <http.//pslgroup.com/dg/2d07e.htm>.
Dodd et al. "Nisin." Abstract.
Dodd et al. "A Cassette Vector For Protein Engineering The Lantibiotic Nisin" *Gene* 162: 163–164 (1995) Abstract.
Rodriguez et al. "Isolation Of Nisin–Producing Lactococcus–Lactis Strains From Dry Fermented Sausages" *Journal of Applied Bacteriology* 78: 109–115 (1995) Abstract.
Dodd et al. "Characterization Of IS905, A New Multicopy Insertion–Sequence Identified In Lactococci", *Journal of Bacteriology* 176: 3393–3396 (1994) Abstract.
Dodd et al. "A Lactococcal Expression system For Engineered Nisins" *Applied And Environmental Microbiology* 58: 3683–3693 (1992) Abstract.
El–Sukhon et al. "Effect of Honey On Bacterial Growth And Spore Germination" *Journal of Food Protection* 57.10: 918–920 (1994) Abstract.
Gordon "Quantitative Determination of Oxytetracycline in Honey By Cylinder Plate Microbioassay" *Australian Journal of Agricultural Research* 40: 933–940 (1989) Abstract.
Lee et al. Studies On The Antibiotic Nisin Produced By Streptococcus Lactis IFO 12007 *Proceedings of the 3$^{rd}$ AAAP Animal Science Congress* 2 (1985) Abstract.
"Inhibit Germination" Nerac, Inc. *Diary Science Abstracts* 48:07349 Abstract.

* cited by examiner

Primary Examiner—Yogendra Gupta
Assistant Examiner—Charles Boyer
(74) Attorney, Agent, or Firm—Reising, Ethington, Barnes, Kisselle, Learman & McCulloch, P.C.

(57) ABSTRACT

Described is An aqueous disinfectant and hard surface cleaning composition comprising:

an effective disinfecting amount of a quaternary ammonium compound;

an effective amount of a spore forming microbial composition; and an effective water dispersing amount of a surfactant.

The composition is used to clean a hard surface containing a diverse microbial flora. The composition cleans and disinfects by killing off undesirable microorganisms which may be causing offensive odors and leaves behind Bacillus spores which will then germinate and degrade any remaining ongoing residues without creating offensive odors.

16 Claims, No Drawings

AQUEOUS DISINFECTANT AND HARD SURFACE CLEANING COMPOSITION AND METHOD OF USE

TECHNICAL FIELD

The present invention is concerned with a disinfecting and hard surface cleaning composition utilizing spore forming microbiological bacteria.

BACKGROUND OF THE INVENTION

In the general housekeeping environment in many facilities, there are numerous soiled surfaces.

In the general housekeeping environment of many facilities, there are numerous surfaces which are difficult for the custodial staff to adequately clean and maintain. The composition and/or function of these surfaces is such that they typically harbor organic soils and a diverse microbial flora that standard cleaning procedures do not effectively remove. Such surfaces include, but are not limited to, floors and walls in areas such as kitchens, restrooms, locker rooms, animal production facilities, kennels or veterinary clinics, loading docks, trash collection bins, and public transit operations.

As these surfaces accumulate soil and the natural microbial flora proliferates due to inadequate cleaning, the facility suffers two consequences. First, apparent cleanliness of the facility diminishes due to the soil load found in these materials. Secondly, this soil load can become a major source of nuisance odors due to the biological degradation of the organics by the resident microbial population.

Current technology does not offer an effective and efficient manner with which to solve this cleaning task. The principle method of cleaning employed relies on a light to medium duty cleaner and/or cleaner/disinfectant.

These types of products are capable of removing most surface soils and in the case of a disinfectant, destroying some of the resident bacterial population. They are not, however, effective against the soils that have penetrated the surface nor does their use of fragrances to mask odor offer any residual control of these nuisances. Because of this, either effective cleaning does not take place or a multi-step process is required to be successful. The best available cleaning technology involves application of the above type product(s) to clean the surface, followed by a rinse of clear water, and the use of a biologically active product to "deep clean" the surface and control odors. Biological products based on bacteria from the genus Bacillus "deep clean" and control odors through the biological degradation of the organics trapped in the substrate.

The objective of this invention is to offer a single-step process by which to accomplish cleaning of these surfaces. The invention is a combination of cleaning, disinfecting, and microbiological activity in one aqueous product.

The utilization of the microbial materials is to destroy offensive odors and their source that may be present on a surface. The purpose of the antimicrobial component is to kill various types of microorganisms found on the surface which might pose health concerns or contribute to nuisance odors. The microbials remain on the surface (after use) to continue the cleaning process through degradation of residual organics. A particularly important aspect of formulating antimicrobial products is that they remain stable for a long period of time. The microbiological materials likewise need to be stable in the presence of the other components of a cleaning composition such as the antimicrobial actives such as the quaternary ammonium compounds.

It is an object of the present invention to obtain an effective disinfectant and hard surface cleaning composition that is aqueous based.

It is an object of the present invention to obtain and utilize in combination a disinfectant, hard surface cleaning, and bacterial composition that is stable for a long period of time, but also allows the microbial material to remain active on the hard surface after the drying of the cleaning composition.

It is an object of the present invention to utilize an aqueous composition containing the genus Bacillus in the presence of disinfectants such as quaternary ammonium compounds.

It is an object of the present invention to perform general cleaning tasks in a more efficient manner whereby the multi-step cleaning process to clean, disinfect and control odors on hard surface substrates is decreased. The utilization of this invention will permit the saving of labor time and reduce chemical inventory.

It is an object of the present invention to utilize compositions that contain a bacterial content that provides better environmental fate attributes to both on site waste treatment systems and municipal treatment plants through biological augmentation of the indigenous bio-mass.

The following references may be pertinent to the invention disclosed herein.

PCT Publication WO97/25865 pertains to a sanitizing composition containing a surfactant, a chelating agent, a preservative, a thickening agent and a Bacillus microorganism.

U.S. Pat. No. 5,449,619 pertains to a drain opener formulation containing a Bacillus microorganism and a surfactant as well as a preservative.

U.S. Pat. No. 4,839,373 pertains to preservative composition containing quaternary ammonium compounds in conjunction with a specific preservative, which is a derivative of benzothiazole in specific ratios.

U.S. Pat. No. 4,404,128 pertains to an enzyme detergent composition where the enzyme is a proteolytic enzyme.

U.S. Pat. No. 4,655,794 pertains to a liquid cleaning compound containing abrasive particles plus viable microorganisms, such as, Bacillus, a detergent, thickener and an anti-settling agent. The composition is a cleaning composition.

U.S. Pat. No. 5,409,546 pertains to a method for cleaning and disinfecting contact lens wherein there is a preservative which is a serine protease derived from bacteria belonging to the genus, Bacillus, a metal chelating agent and boric acid. Non-ionic surfactants are also described.

U.S. Pat. No. 5,731,278 describes heavy-duty laundry detergents containing surfactants, non-surface active liquid carrier compositions, viscosity enhancing agents and enzymes.

PCT publication WO97/16541 described an alkaline protease, which describes a strain of Bacillus and which shows a stability in the presence of surfactants.

PCT publication WO97/38586 discloses a method of preventing the growth of microorganisms other than Salmonella on meat products by contacting the meat product with a microbial growth inhibiting amount of a quaternary ammonium compound together with a microorganism, such as Bacillus.

SUMMARY OF THE INVENTION

Described is an aqueous disinfectant and hard surface cleaning composition comprising:

an effective disinfecting amount of a quaternary ammonium compound;

an effective amount of a spore forming microbial composition; and an effective water dispersing amount of a surfactant.

Also described is a method of cleaning a soiled hard surface containing a diverse microbial flora, comprising applying the composition as described above to the surface and drying the surface thereby cleaning the surface.

Also described is a concentrated aqueous disinfectant and hard surface cleaning composition described above useful by diluting the composition with water in an amount of 1–10% by weight of the composition and the rest water.

DESCRIPTION OF PREFERRED EMBODIMENTS

The aqueous disinfectant and hard surface cleaning composition of the present invention utilizes an effective disinfecting amount of a quaternary ammonium compound. The ammonium compound is a cationic detergent which provides excellent activity against bacteria, fungi and enveloped viruses. Additionally, quaternaries offer consistent efficacy in the presence of poor water quality and organic soil load conditions. For a more detailed listing of enveloped viruses, see Fields Virology, $2^{nd}$ Edition 1990.

Antimicrobial cationics available to the trade.

There are three principal suppliers of quaternary based antimicrobials that are registered as actives for this type of use with the EPA. These companies are Lonza, Stepan and Mason Chemical Company. The trade names under which they are marketed are Bardac, BTC and Maquat respectively. All of the desirable cationic material sold conform to one of the following families:

| First Generation: | $C_6H_5$—$CH_2N(CH_3)_2R$ Alkyldimethylbenzyl ammonium chloride |
| Second Generation: | $(C_2H_5)C_6H_5$—$CH_2N(CH_3)_2R$ Alkyldimethylethylbenzyl ammonium chloride |
| Third Generation: | $N(R)_2(CH_3)_2$ R-dimethyl ammonium chloride |

The preferred cationic detergent is from the quaternary ammonium chloride family such as the BTC (trademark) materials from Stepan Chemical including dialkyl of from 6–18 carbon atoms dialkyl of from 1–4 carbon atoms ammonium chloride; preferably didecyl dimethyl ammonium chloride, dioctyl dimethyl ammonium chloride, octyl decyl dimethyl ammonium chloride and alkyl ($C_{14}$—50%, $C_{12}$—40%, $C_{16}$—10%) dimethyl benzyl ammonium chloride. Even more preferably is a blend of the ammonium chloride materials as recited below.

The system utilized in this product is designed to maximize all of the beneficial aspects of quaternary ammonium compounds and consists of the following blend in a 1:1:2:2.67 wt. ratio respectively:

1. Didecyl dimethyl ammonium chloride (BTC818) (Trademark of Stepan Chemical)
2. Dioctyl dimethyl ammonium chloride (BTC818) (Trademark of Stepan Chemical)
3. Octyl decyl dimethyl ammonium chloride (BTC818)
4. Alkyl ($C_{14}$—50% by wt, $C_{12}$—40% by wt, $C_{16}$—10% by wt) dimethyl benzyl ammonium chloride. (BTC835) (Trademark of Stepan Chemical)

During use as a disinfecting composition, the total levels of this blend (1–4) will preferably range from 500 to 1000 ppm's (parts by weight per million).

Other quaternary materials that may be utilized are Tomah quaternaries (trademark of Tomah Products of Milton, Wis. for quaternary ammonium materials).

Tomah quaternaries are based on the reaction of high molecular weight aliphatic tertiary amines with an alkylating agent such as methyl chloride. Quaternaries are more cationic and more stable to pH change than other amine-based surfactants such as ethoxylated amines or amine acetate salts. The different molecular configurations give different solubility, emulsification, and cationic strength properties.

Most Tomah Quaternaries can be represented by the formula where R is an aliphatic hydrophobe.

$$RO(CH_2)_3N^+(CH_3)(C_2H_4OH)_2Cl^-$$

R is an aliphatic alkyl of hydrophobe (of from 6–18 carbon atoms)

Other useful quaternary ammonium materials from Tomah are:

| Q-14-2 | 75% active isodecyloxypropyl dihydroxyethyl methyl ammonium chloride; |
| Q-14-2PG | 75% active isodecyloxypropyl dihydroxyethyl methyl ammonium chloride (supplied in propylene glycol); |
| Q-17-2 | 75% active isotridecyloxypropyl dihydroxyethyl methyl ammonium chloride; |
| Q-17-2PG | 75% active isotridecyloxypropyl dihydroxyethyl methyl ammonium chloride (supplied in propylene glycol); |
| Q-18-2 (50) | 50% active octadecyl dihydroxyethyl methyl ammonium chloride; |
| Q-18-15 | 100% active octadecyl poly(15)oxyethylene methyl ammonium chloride; |
| Q-D-T | 50% active tallow diamine diquaternary; |
| Q-DT-HG | 70% active tallow diamine diquaternary (supplied in hexylene glycol); |
| Q-C-15 | 100% active coco poly(15)oxyethylene methyl ammonium chloride; and |
| Q-ST-50 | 50% active trimethyl stearyl quaternary ammonium material. |

The present invention utilizes an effective amount of a spore forming microbial composition. The biological products that are desirable with the present invention are in liquid or lyophilized form and are generally based upon the bacteria from the genus Bacillus. These organisms are preferred because they are easy to be formulated due to their ability to go into a dormant spore state. In addition, the organic degradation abilities of certain species within the Bacillus genus are appropriate for the types of applications described herein for cleaning purposes. Further, the Bacillus bacteria lend themselves readily to large scale fermentation. The bacterial content of the formulations as described herein are desirable based upon their stability in the presence of the other components of the formulation, in particular, the antimicrobial quaternary materials. Preferred organisms are *Bacillus amyloliquefaciens, Bacillus licheniformis, Bacillus megaterium* and *Bacillus subtilis*. These products are commercially available from a number of sources. The preferred materials of the Bacillus genus can be obtained from Semco Laboratories, Inc. available under the name Sporzyme 1B, Sporzyme Ultra Base 2, Sporzyme EB and Sporzyme BCC (all trademarks of Semco Laboratories for liquid materials containing bacterial spores of the Bacillus genus). The Bacillus genus materials are also available from Sybron Chemicals, Inc. of Wilmington, Del.

An additional component utilized in the disinfectant leaning composition of the present invention is a surfactant. The use of surfactants is to assist in decreasing the surface tension of water and remove soils from the substrate. A particularly desirable group of surfactants are those that maintain the stability of the cationic disinfectant and the microbiological materials. The surfactants that are preferably utilized are non-ionic and amphoteric materials. These materials provide efficient wetting of the substrate to be cleaned, emulsification of oily soils and are ionically compatible with the cationic components of the cleaning composition.

Non-ionic materials that may be utilized include fatty amines or oxides, fatty alkanolamides, alkyl polyglucosides and linear alcohol ethoxylates. Preferred surfactants are secondary alcohol ethoxylates, betaines, sultaines and amine oxides. Preferred alcohol ethoxylates and ethoxysulfates are available under the trademark Neodol Chemical Company (trademark for surfactants of Shell). Neodol products include linear primary alcohols in a $C_9$–$C_{15}$ alkyl range, ethoxylate non-ionic surfactants and ethoxy sulfate.

Further examples of non-ionic surfactants are materials known as Igepal (trademark of Rhodia, Inc. for nonyl phenoxy polyethoxy ethanol); Tergitol NP (trademark of Union Carbide Corp. for nonylphenol ethoxylate); Tergitol 15-S (trademark of Union Carbide Corp. for secondary alcohol ethoxylates); Triton X series (trademark of Union Carbide Corp. for octyl phenol polyethoxylate) and Tween Materials (trademark of ICI Americas, Inc. for polyoxyethylene (20) sorbitan monostearate and polyoxyethylene sorbitan monooleate). Examples of amphoteric materials include Mirataine CBC and Miranol C2MSF (trademark of Rhodia, Inc. for surfactant) and Lexaine (trademark of Inolex Co. for cocoamidopropyl betaine).

In order to maintain the stability of the dispersion of the microbiological spores that are utilized in the present case and to prevent the spores from settling out, which causes a loss in the effectiveness of a product, thickening agents are utilized. The thickening agents that are desirable are those that are compatible with cationic systems. A preferred thickening agent is a cellulosic material such as hydroxyethylcellulose. Preferred are Natrosol (trademark of Hercules for non-ionionic water soluble polymer hydroxylethyl cellulose) and Cellosize (Trademark of Union Carbide for hydroxymethylcellulose).

An additional thickening agent that may be used is Acusol 880/882—(Trademark of Rohm and Haas Co. for nonionic associative polymer mixture of polyethylene glycol, propylene glycol and water having a pH of 7–9 and a viscosity of 60,000 CPS maximum).

The formulation for cleaning composition of the present application is as follows:

| NAME | CONCENTRATE AMOUNT (% by wt.) | PREFERRED AMOUNT FOR USE |
|---|---|---|
| Cationic Material | 1–10%, preferably 5.5% | 0.1–2%, preferably 0.085% |
| Microbiological Material | $1 \times 10^9$ - $1 \times 10^{12}$, preferably $5.0 \times 10^{11}$ CFU/gallon | $1 \times 10^8$ - $1 \times 10^{10}$, preferably $7.8 \times 10^9$ CFU/gallon |
| Surfactant | 1–10%, preferably 6.53% | 0.1 to 5% |
| Thickening Agent | 0.01–2.0%, preferably 0.25% | (0.0002–0.005%) trace |
| Remaining Amount: Water | Total 100% | |

The pH of the composition in the concentrate form ranges from about 6 to 8. The pH in the composition as actually used ranges from about 7 to 8.

The preferred formulation is recited below. The composition is prepared by mixing the ingredients as described.

TABLE I

| Formula (% by wt.) | | |
|---|---|---|
| Water | 50.00% | pH-8.0 +/− 0.2% |
| Natrosol 250 HR (hydroxyethyl cellulose thickener) | 0.25% | *RIS-13.0% +/− 0.2% |
| 45% Potassium Hydroxide | 0.0225% | Specific Gravity −0.999 |
| Sodium Chloride | 0.2% | |
| Q-17-2 (Quaternary) | 1.7% | |
| Neodol 25-7 (non-ionic surfactant) | 5% | |
| BTC 818 (Quaternary) | 6.53% | |
| BTC 835 (Quaternary) | 4.35% | |
| Fragrance | 0.15% | |
| Citric Acid | 0.01% | |
| Water | 31.87% | |
| Bacteria Cultures | 0.01% | |
| Dye | 0.002% | |

*RIS means refractive index of solids.

Mixing instructions:

Add the ingredients in the order above. First, add the water and disperse the Natrosol 250 HR slowly and evenly to the water. Avoid large clumps of Natrasol 250 HR. Once the total amount of the Natrosol 250 HR has been added, add the potassium hydroxide to the solution. Mix well for approximately ten minutes or until the Natrosol 250 HR is hydrated. After the Natrosol 250 HR has been hydrated continue by adding the salt, and mix for two minutes, or until dissolved. Next, add the Q-17-2 and the Neodol 25-7, mix well for ten minutes or until there are no chunks of undispersed surfactant. Continue by adding the BTC818 and the BTC 835. After the surfactants are dispersed, add the fragrance and mix until solution becomes clear. Before adding the Bacterial cultures adjust the pH by adding the citric acid. Finally, mix the final water and the bacterial cultures in a separate container. When the Bacterial cultures are completely hydrate, add to the batch. Last, add the dye and mix until dispersed thoroughly.

The formulation as described above in Table I was subjected, to bacterial stability tests, namely subjecting the composition to long term stability at room temperature and at a hot box temperature of 100° F.

The Table II below indicates the long term stability of the composition of the invention.

TABLE II

| Days | 0 | 7 | 17 | 27 | 34 | 41 | 45 | 46 | 52 | 60 | 87 | 100 |
|---|---|---|---|---|---|---|---|---|---|---|---|---|
| Room* Temp CFU | 2.63 | 2.6 | 2.7 | 2.5 | 2.23 | 1.6 | 4.37 | 2.2 | 2.33 | 2.45 | 1.87 | 1.9 |
| 100° F.* CFU | 2.63 | | 0.4 | 1.1 | 1.17 | 1.05 | 0.43 | 2.17 | 0.53 | 0.57 | 1.0 | 0.4 |

CFU = Colony Forming Unit ($\times 10^7$)
*Data given at room temperature and at 100° F.

The compositions of the present application can easily be utilized to meet the cleaning performance requirements of different testing techniques. An example of such testing technique is a cleaning verification as described in ASTM D 4488-95 where the natural or accelerated aging of soil such as baked on greasy soil may be utilized to correlated with actual use. Other actual use tests to determine antimicrobial efficacy are the SARC (semi-automatic ring carrier) modification to and actual AOAC use-dilution method for testing disinfectants. See the AOAC Official Methods Of Analysis, 15$^{th}$ Edition, 1990.

It has been found particularly useful in the testing of Applicant's compositions to utilize nisin in a modification to the AOAC method compositions. Nisin is an antibiotic containing 34 amino acid residues, produced by streptomyces lactis.

Explanation of Nisin:

Nisin is not an ingredient in the product formulation. It is a modification to the AOAC test method. Specifically, when setting up the test sub-culture 0.1 µg/ml of nisin is added to the letheen broth. This level of nisin shows no bacteriostatic effect on the test organism, but inhibits out-growth of any Bacillus spores which are transferred over on the carrier from the test solution.

The standard "use-dilution" test was run against *Staphylococcus aureus, Pseudomonas aeruginosa, Salmonella choleraesuis* and *Escherichia coli*. The inventive composition described in Table I satisfactorily passed such tests.

Other components may be added to the composition without materially modifying the composition such as colorant and fragrance.

The composition as described above is particularly useful for the overall desires of the present application for cleaning and disinfecting hard surfaces.

While the forms of the invention herein disclosed constitute presently preferred embodiments, many others are possible. It is nol intended herein to mention all of the possible equivalent forms or ramifications of the invention. It is understood that the terms used herein are merely descriptive rather than limiting, and that various changes may be made without departing from the spirit or scope of the invention.

What is claimed is:

1. An aqueous disinfectant and hard surface cleaning composition consisting essentially of:
   an effective disinfecting amount of a quaternary ammonium compound;
   an effective spore forming amount of a Bacillus microbial composition; and
   an effective water dispersing amount of a surfactant other than the quaternary ammonium compound.

2. A concentrated aqueous disinfectant and hard surface cleaning composition, useful by diluting with water, consisting essentially of:
   an effective disinfecting amount of a quaternary ammonium compound;
   an effective spore forming amount of Bacillus microbial composition;
   an effective water dispersing amount of [an additional material,] a surfactant other than the quaternary ammonium compound; and
   an effective thickening amount of a thickening agent.

3. The composition of claim 1 wherein the cleaning composition is present in the amount of 1 to 10% by wt. with the remainder of the composition being 90 to 99% by wt water.

4. The composition of claim 3 wherein the quaternary ammonium compound is present in the amount of 5.5%;
   the spore forming microbial composition is present in the amount of 0.01%;
   the additional surfactant is present in the amount of 6.3%; and the pH ranges from 6 to 8.

5. The composition of claim 1 consisting essentially of the following materials by weight:

| | |
|---|---|
| quaternary ammonium material | 1–10% |
| Bacillus microbial material | $1 \times 10^9$–$1 \times 10^{12}$ CFU/gallon (colony forming unit) |
| additional surfactant | 1–10% |
| a thickening agent | 0.1–5% |
| Water | remaining amount total 100%. |

6. The composition of claim 1 consisting essentially of the following materials:

| | |
|---|---|
| quaternary ammonium material | 0.1–2% by wt. |
| Bacillus microbial material | $1 \times 10^8$–$1 \times 10^{10}$ CFU/gallon |
| additional surfactant | 0.1–5% |
| a thickening agent | trace |
| water | remaining amount total 100%. |

7. A method of cleaning a soiled hard surface containing a diverse microbial flora comprising applying the composition of claim 1 to the surface and drying the surface, thereby cleaning and disinfecting the surface.

8. The method of claim 7 wherein the hard surface contains microbes, selected from the group consisting of *Staphylococcus aureus, Pseudomonas aeruginosa, Salmonella choleraesius* and *Escherichia coli*.

9. The method of claim 7 wherein the soiled surface is comprised of blood serum as an organic soil load in the composition which is diluted in hard water containing 100–400 ppm $CaCO_3$, thereby demonstrating efficacy as a one-step cleaner disinfectant.

10. The method of claim 7 consisting essentially of the following materials:

| quaternary ammonium material | 1–10% |
|---|---|
| Bacillus microbial material | $1 \times 10^9$- $1 \times 10^{12}$ CFU/gallon (colony forming unit) |
| additional surfactant | 1–10% |
| a thickening agent | 0.1–5% |
| water | remaining amount total 100%. |

11. The method of claim 7 consisting essentially of the following materials:

| quaternary ammonium material | 0.1–2% by wt. |
|---|---|
| Bacillus microbial material | $1 \times 10^8$-$1 \times 10^{10}$ CFU/gallon |
| additional surfactant | 0.1–5% |
| a thickening agent | trace |
| water | remaining amount total 100%. |

12. An aqueous disinfectant and hard surface cleaning composition consisting essentially of by weight:

| A quaternary a spore forming ammonium material | 1–10% |
|---|---|
| Bacillus microbiological material | $1 \times 10^9$-$1 \times 10^{12}$ CFU/gallon |
| an additional the quaternary ammonium surfactant other than | 1–10% |
| thickening agent | 0.1–5% |
| water | remaining amount total 100% | wherein the above composition being stable at room temperature and 100° F. for at least 45 days.

13. The composition of claim 1, wherein the quaternary ammonium compound is a dialkyl of from 6–18 carbon atoms, dialkyl of 1 to 4 carbon atoms ammonium compound.

14. The composition of claim 2, wherein the quaternary ammonium compound is a dialkyl of from 6–18 carbon atoms, dialkyl of 1 to 4 carbon atoms ammonium compound.

15. The composition of claim 1, wherein the Bacillus material is comprised of *Bacillus subtilis*.

16. The composition of claim 2, wherein the Bacillus material is comprised of *Bacillus subtilis*.

* * * * *

UNITED STATES PATENT AND TRADEMARK OFFICE
CERTIFICATE OF CORRECTION

PATENT NO. : 6,180,585 B1
DATED : January 30, 2001
INVENTOR(S) : William John Schalitz et al.

It is certified that error appears in the above-identified patent and that said Letters Patent is hereby corrected as shown below:

Column 8,
Lines 16-17, after "dispersing amount of" delete "an additional material,"

Column 10,
Line 3, after "A quaternary" delete "a spore forming"
Line 5, before "Bacillus" insert therein -- "A spore forming" --
Lines 6-7, after "an additional" delete "the quaternary ammonium"; after "other than" insert therein -- "the quaternary ammonium surfactant" --

Signed and Sealed this

Twenty-ninth Day of January, 2002

Attest:

*Attesting Officer*

JAMES E. ROGAN
*Director of the United States Patent and Trademark Office*